United States Patent
Wang (10) Patent No.: US 7,136,160 B2
(45) Date of Patent: Nov. 14, 2006

(54) INTEGRATED SYSTEM AND METHOD FOR TRANSVERSAL ENHANCED RAMAN SPECTROSCOPY

(75) Inventor: Shih-Yuan Wang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 165 days.

(21) Appl. No.: 11/044,781

(22) Filed: Jan. 27, 2005

(65) Prior Publication Data

US 2006/0164637 A1    Jul. 27, 2006

(51) Int. Cl.
G01J 3/44        (2006.01)
G01N 21/65       (2006.01)

(52) U.S. Cl. .......................................... 356/301; 385/12
(58) Field of Classification Search ................. 356/301
See application file for complete search history.

(56) References Cited

U.S. PATENT DOCUMENTS

| | | | |
|---|---|---|---|
| 5,002,350 A | 3/1991 | Dragone | |
| 5,455,421 A | 10/1995 | Spears | |
| 6,380,531 B1 | 4/2002 | Sugihwo et al. | |
| 6,613,600 B1 | 9/2003 | Tran et al. | |
| 6,690,851 B1 | 2/2004 | Guilfoyle | |
| 6,726,763 B1 | 4/2004 | Lee et al. | |
| 6,775,308 B1 | 8/2004 | Hamster et al. | |
| 6,782,027 B1 | 8/2004 | Cox et al. | |
| 6,795,623 B1 | 9/2004 | Duan et al. | |
| 2002/0018504 A1 | 2/2002 | Coldren | |
| 2004/0021860 A1 | 2/2004 | Gardner et al. | |

FOREIGN PATENT DOCUMENTS

| | | |
|---|---|---|
| GB | 2408796 | 6/2005 |
| WO | WO 00/43754 | 7/2000 |
| WO | WO 02/079821 | 10/2002 |
| WO | WO 2006/010367 | 2/2006 |
| WO | WO 2006/027581 | 3/2006 |

OTHER PUBLICATIONS

Borgulova, J., et al., "Design of a Tunable RCE Photodetector for the 1550 nm Wavelength Range," ASDAM '98, 2nd International Conference on Advanced Semiconductor Devices and Microsystems, Smolenice Castle, Slovakia, Oct. 5-7, 1998, pp. 117-120.

(Continued)

*Primary Examiner*—F. L. Evans (57) ABSTRACT

Devices and methods for enhancing Raman Spectroscopy are disclosed. A molecular analysis device for performing Raman spectroscopy comprises a substrate and a laser source disposed on the substrate. The laser source is configured for generating a laser radiation with a direction substantially parallel with the substrate. The molecular analysis device also includes a Raman enhancement structure, which may be disposed on the substrate or on a waveguide disposed on the substrate. The Raman enhancement structure has an active surface substantially parallel to the substrate and is configured for producing a Raman scattered radiation. The Raman scattered radiation may be produced, when the laser radiation irradiates an analyte disposed on the Raman enhancement structure, or when an evanescent field emanating from the waveguide irradiates an analyte disposed on the Raman enhancement structure. In addition, a radiation receiver disposed on the substrate is configured for receiving the Raman scattered radiation.

52 Claims, 4 Drawing Sheets

OTHER PUBLICATIONS

Emsley, Matthew K., et al., "High-Speed Resonant-Cavity-Enhanced Silicon Photodetectors on Reflecting Silicon-On-Isulator Substrates," IEEE Photonics Technology Letters, vol. 14, No. 4, Apr. 2002, pp. 519-521.

Emsley, Matthew K., et al., "Silicon Substrates With Buried Distributed Bragg Reflectors for Resonant Cavity-Enhanced Optoelectronics," IEEE Journal of Selected Topics in Quantum Electronics, vol. 8, No. 4, Jul./Aug. 2002, pp. 948-955.

Jlang, Jiang, et al., "Single Molecule Raman Spectroscopy at the Junctions of Large Ag Nanocrystals," J. Phys. Chem. B, vol. 107, No. 37, 2003, pp. 9964-9972.

Kelley, Anne Myers, et al., "Resonance Hyper-Raman Scattering from Conjugated Organic Donor-Acceptor "Push-Pull" Chromophores with Large First Hyperpolarizabilities," J. Am. Chem. Soc., vol. 125, No. 35, 2003, pp. 10520-10521.

Kishino, Katsumi, et al., "Resonant Cavity-Enhanced (RCE) Photodetectors," IEEE Journal of Quantum Electronics, vol. 27, No. 8, Aug. 1991, pp. 2025-2034.

Purica, M., et al., "Analysis and Optimization of the Bragg Reflector for Tunable Photodetector with Planar Mirror Optical Microcavity on Silicon Substrate," IEEE, 2003, pp. 155-158.

Smit, Meint K., et al., "PHASAR-Based WDM-Devices: Principles, Design and Applications," IEEE Jouranal of Selected Topics in Quantum Electronics, vol. 2, No. 2, Jun. 1996, pp. 236-250.

Yelin, Dvir, et al., "Multiphoton plasmon-resonance microscopy," Optics Express, vol. 11, No. 12, Jun. 16, 2003, pp. 1385-1391.

Song et al —"Photonic Devices Based on In-Plane Hetero Photonic Crystals"—Science vol. 300 Jun. 6, 2003 —p. 1537.

INTEGRATED SYSTEM AND METHOD FOR TRANSVERSAL ENHANCED RAMAN SPECTROSCOPY

CROSS REFERENCE TO RELATED APPLICATIONS

The present application is related to concurrently filed U.S. patent application Ser. No. 11/044,421 entitled MONOLITHIC SYSTEM AND METHOD FOR ENHANCED RAMAN SPECTROSCOPY, and concurrently filed U.S. patent application Ser. No. 11/044,676 entitled INTEGRATED MODULAR SYSTEM AND METHOD FOR ENHANCED RAMAN SPECTROSCOPY.

FIELD OF THE INVENTION

The present invention relates to chemical analysis using Raman spectroscopy. More particularly, the present invention relates to integrated systems for Raman Spectroscopy combining a radiation source and Raman scattered radiation sensing. In addition, the present invention relates to hyper-Raman, where the excitation wavelength is approximately an integer multiple of the Raman wavelength.

BACKGROUND OF THE INVENTION

Raman Spectroscopy is a well-known spectroscopic technique for performing chemical analysis in the gas, liquid or solid phase. In conventional Raman Spectroscopy, high intensity monochromatic light from a light source, such as a laser, is directed onto an analyte to be chemically analyzed. The analyte may contain a single species of molecules or mixtures of different molecules. Furthermore, Raman Spectroscopy may be performed on a number of different molecular configurations, such as organic and inorganic molecules in crystalline or amorphous states.

For a system that does not have surface or nanostructure enhancement, the majority of the incident photons of the light are elastically scattered by the analyte molecule. In other words, the scattered photons have the same frequency, and thus the same energy, as the photons that were incident on the analyte. This is known as Rayleigh scattering. However, a small fraction of the photons (i.e., 1 in $10^7$ photons) are inelastically scattered by the unenhanced analyte molecule at a different optical frequency than the incident photons. The inelastically scattered photons are termed the "Raman scattered radiation" and may be scattered at frequencies greater than, but most are usually scattered at a frequency lower than, the frequency of the incident photons. When the incident photons collide with the molecules and give up some of their energy, the Raman scattered photons (also referred to as Raman scattered radiation) emerge with a lower energy. The lower energy Raman scattered photons are commonly referred to in Raman spectroscopy as the "Stokes radiation." A small fraction of the molecules are already in an energetically excited state and when the incident photons collide with the molecules, the Raman scattered photons emerge at a higher energy and thus at a higher frequency. The higher energy Raman scattered photons are commonly referred to in Raman spectroscopy as the "anti-Stokes radiation." Raman scattering may occur from the rotational, vibrational, or electronic states of the molecules.

The Stokes and the anti-Stokes Raman scattered photons are collected using optics, the different frequencies are dispersed spatially with some type of spectrometer, and the photons are registered by a detector, such as a photomultiplier, resulting in a spectral graph of intensity at a corresponding frequency (i.e., proportional to energy) for the Raman scattered photons. By plotting the intensity of the inelastically scattered Raman photons against frequency, a unique Raman spectrum, which corresponds to the particular analyte molecules, is obtained. This Raman spectrum may be used to identify chemical species, as well as other physical properties of the analyte. While conventional Raman Spectroscopy is suitable for bulk chemical analysis, it is not effective for surface studies because the signal from the bulk Raman scattered photons overwhelms any signal from Raman scattered photons near the surface.

In hyper-Raman spectroscopy, when excitation radiation impinges on an analyte molecule, a very small number of photons may be scattered at frequencies corresponding to the higher order harmonics of the excitation radiation, such as the second and third harmonics (i.e., twice or three times the frequency of the excitation radiation). Some of these photons may be Raman scattered photons with a frequency that is Raman-shifted relative to the frequencies corresponding to the higher order harmonics of the excitation radiation. Therefore, in hyper-Raman spectroscopy, the incident excitation photons have approximately $\frac{1}{2}$, $\frac{1}{3}$, or $\frac{1}{4}$ the frequency of the Raman photons.

Due to the deficiencies with performing surface studies using conventional Raman Spectroscopy, another Raman Spectroscopy technique called Surface Enhanced Raman Spectroscopy (SERS), which is effective for performing surface studies, has been developed. In SERS, a monolayer or sub-monolayer amount of the molecules to be analyzed is adsorbed onto a specially roughened metal surface. Typically, the metal surface is made from gold, silver, copper, lithium, sodium, or potassium. Raman spectroscopy has also been used employing metallic nanoparticles or nanowires for the metal surface, as opposed to a roughened metallic surface, which is hereinafter referred to as Nano-Enhanced Raman Spectroscopy (NERS). The intensity of the Raman scattered photons from a collection of molecules adsorbed on such a metal surface is typically about $10^4$–$10^6$ greater than conventional Raman Spectroscopy from a similar number of molecules in a bulk specimen, and can be as high as $10^8$–$10^{14}$ for a single molecule adsorbed near two or more metal nanoparticles. Although not thoroughly understood, the selectivity of the surface Raman signal results from the presence of surface enhancement mechanisms and is mainly attributed to two primary mechanisms: electromagnetic enhancement and chemical enhancement, with the electromagnetic enhancement being the dominant mechanism. The enhanced electromagnetic field is highly dependent on the surface roughness features of the enhancement surface. The chemical enhancement is believed to be dependent on the altered electronic structure of the enhancement surface due to adsorption of the analyte. The enhanced electromagnetic field of the enhancement surface, which is adjacent to the analyte, irradiates the analyte, producing an enhanced Raman signal having a strength that is, in part, proportional to the square of the enhanced electromagnetic field. Thus, Raman spectroscopy may be used to study monolayers of materials adsorbed on metals, and even single molecules adsorbed near an appropriate metal nanostructure (i.e., NERS).

In a conventional SERS system, a spectrometer collects all radiation, including the Stokes radiation, anti-Stokes radiation, and the elastically scattered radiation, and provides a spectrum of the scattered radiation. The spectrum may then be used to identify the chemical species, as well as other physical properties of the analyte. Conventionally, the spectrometer may include various optical elements such as lenses, gratings, photomultipliers, and filters. While this arrangement may be flexible, it is often bulky, expensive, and requires significant user interaction to analyze a chemical species.

An integrated Raman spectroscopy analysis system, which integrates a laser light source, a Raman enhancement structure, and a radiation detection element, may be a smaller and less costly system. In addition, a Raman spectroscopy analysis system that irradiates the Raman enhancement structure from a laser light source that has a direction substantially parallel to the Raman enhancement structure may provide radiation across a larger surface area of the Raman enhancement structure, and, as a result, generate additional Raman scattered radiation. This integrated Raman spectroscopy analysis system may be easier to use and may be adaptable to detection of a predetermined set of molecules.

BRIEF SUMMARY OF THE INVENTION

The present invention, in a number of embodiments, includes devices for generating Raman scattered radiation, Surface Enhanced Raman Spectroscopy (SERS) systems, Nano-Enhanced Raman Spectroscopy (NERS) systems, and methods of performing SERS and NERS.

In one aspect of the present invention, a molecular analysis device comprises a substrate and a laser source disposed on the substrate. The laser source is configured for generating a laser radiation with a direction substantially parallel with the substrate. The molecular analysis device also includes a Raman enhancement structure disposed on the substrate. The Raman enhancement structure has an active surface substantially parallel to the substrate and is configured for producing a Raman scattered radiation when the laser radiation irradiates an analyte disposed on the Raman enhancement structure. In addition, a wavelength demultiplexer disposed on the substrate is configured for dispersing the Raman scattered radiation into at least two unique wavelengths, and at least two radiation sensors disposed on the substrate are configured for sensing one of the at least two unique wavelengths.

In another embodiment, a molecular analysis device comprises a substrate and a laser source disposed on the substrate. The laser source is configured for generating a laser radiation with a direction substantially parallel with the substrate. The molecular analysis device also includes a waveguide disposed on the substrate and configured for generating an evanescent field when the laser radiation is present in the waveguide. The molecular analysis device also includes a Raman enhancement structure disposed on the waveguide. The Raman enhancement structure is configured for producing a Raman scattered radiation when the evanescent field irradiates an analyte disposed on the Raman enhancement structure. In addition, a wavelength demultiplexer disposed on the substrate is configured for dispersing the Raman scattered radiation into at least two unique wavelengths, and at least two radiation sensors disposed on the substrate are configured for sensing one of the at least two unique wavelengths.

Other embodiments of the present invention include methods for performing Raman spectroscopy. One method of performing Raman spectroscopy comprises generating a laser radiation from a laser source disposed on a substrate. The laser radiation has a direction substantially parallel with the substrate and a Raman enhancement structure disposed over at least a portion of the substrate such that the laser radiation is directed over a surface of the Raman enhancement structure. The method further includes disposing an analyte over at least a portion of the surface of the Raman enhancement structure and irradiating the analyte and the Raman enhancement structure with the laser radiation to generate a Raman scattered radiation. With the Raman scattered radiation generated, the method further includes dispersing the Raman scattered radiation into at least two unique wavelengths and sensing the at least two unique wavelengths with at least two radiation sensors disposed on the substrate.

In yet another embodiment, a method of performing Raman spectroscopy comprises generating a laser radiation from a laser source disposed on a substrate. The laser radiation is directed at a waveguide disposed substantially parallel with the substrate and on at least a portion of the substrate. The method further includes disposing an analyte over at least a portion of a surface of a Raman enhancement structure disposed on at least a portion of a surface of the waveguide. In addition, the method includes generating an evanescent field, which emanates from the surface of the waveguide when the waveguide is irradiated by the laser radiation. The evanescent field, irradiating the analyte and the Raman enhancement structure, generates a Raman scattered radiation. With the Raman scattered radiation generated, the method further includes dispersing the Raman scattered radiation into at least two unique wavelengths and sensing the at least two unique wavelengths with at least two radiation sensors disposed on the substrate.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes structures and devices for use in Surface Enhanced Raman Spectroscopy (SERS) systems, Nano-Enhanced Raman Spectroscopy (NERS) systems and methods of performing SERS and NERS. Systems that may incorporate SERS and NERS techniques are generally referred to herein as employing Enhanced Raman Spectroscopy (ERS). As shown in the figures and described in further detail below, molecular analysis structures and molecular analysis devices of the present invention incorporate a laser source, a Raman enhancement structure, a wavelength demultiplexer, and a radiation receiver on a substrate. In some embodiments, the Raman enhancement structure may be disposed on the substrate, while in other embodiments the Raman enhancement structure may be disposed on a waveguide, which is disposed on the substrate. In addition, the sensitivity of Raman spectroscopy systems of the present invention may be enhanced by the type of surface on the Raman enhancement structure to enable more accurate and sensitive detection of chemical species and other physical properties of the sample being analyzed, including single molecule detection. Furthermore, the Raman spectroscopy systems of the present invention may be employed as an analytical instrument for detecting specific chemicals.

Figure 1A:
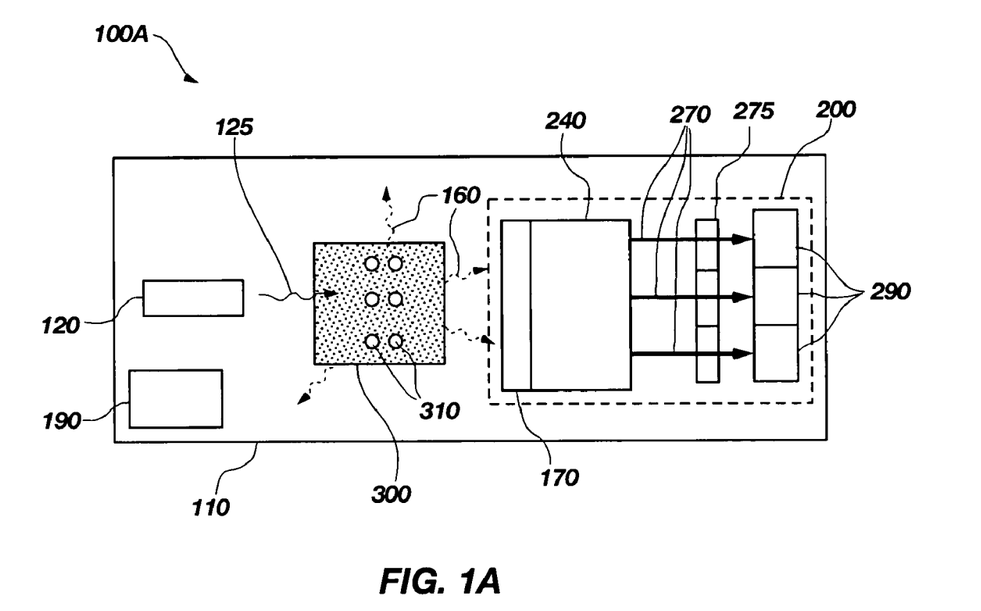
FIG. 1A is a top view of an exemplary molecular analysis device including a Raman enhancement structure disposed on a substrate.
Figure 1B:
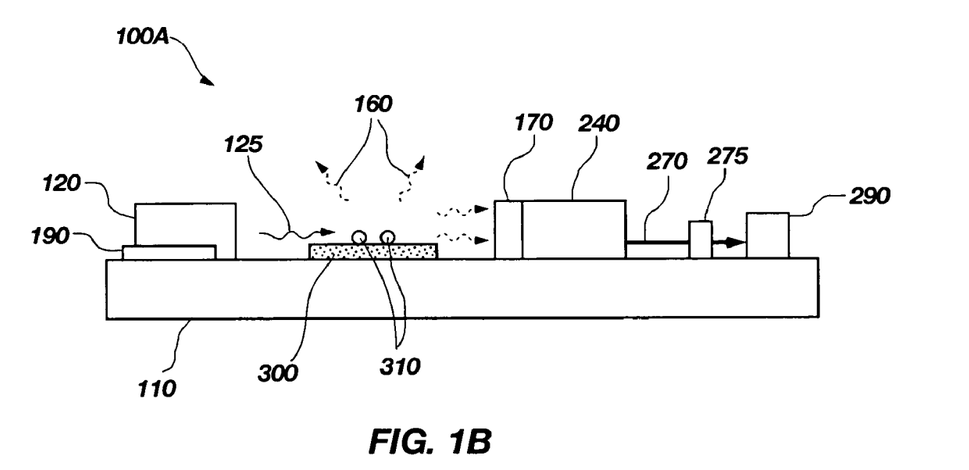
FIG. 1B is a side view of the molecular analysis device of FIG. 1A.

FIGS.1A, and 1B illustrate an exemplary embodiment of a molecular analysis device 100A (also referred to as a direct irradiation device 100A) employing ERS. The direct irradiation device 100A includes the substrate 110, the laser source 120 disposed on the substrate 110, the wavelength demultiplexer 240 disposed on the substrate 110, and the radiation receiver 200 disposed on the substrate 110. In addition, the Raman enhancement structure 300 is disposed on the substrate 110 such that the active surface is substantially parallel with the surface of the substrate 110. An optional filter 170 may also be disposed on the substrate 110 between the Raman enhancement structure 300 and the wavelength demultiplexer 240. The direct irradiation device 100A may also include other optional components 190. This embodiment may be used as a self-contained Raman spectroscopy analysis system wherein an analyte 310 may be disposed on the Raman enhancement structure 300 on the substrate 110.

In operation, the laser source 120 emits a laser radiation 125 in a direction that is substantially parallel to the active surface of the Raman enhancement structure 300 and positioned to irradiate the Raman enhancement structure 300 and analyte 310 disposed on the Raman enhancement structure 300, as shown in FIGS. 1A and 1B. In this fashion, the laser radiation 125 may irradiate the analyte 310 and Raman enhancement structure 300 across the entire length of the Raman enhancement structure 300. The irradiated combination of the Raman enhancement structure 300 and the analyte 310 may generate Raman scattered radiation 160. The Raman scattered radiation 160 may be detected as a variety of wavelengths by the radiation receiver 200, as explained more fully below.

Figure 2A:
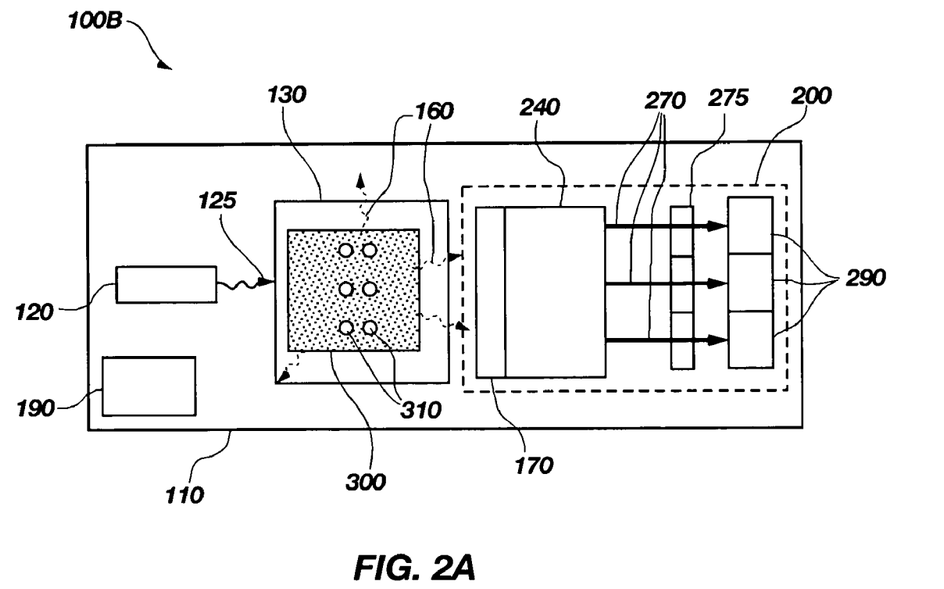
FIG. 2A is a top view of an exemplary embodiment of a molecular analysis device including the Raman enhancement structure on a waveguide.
Figure 2B:
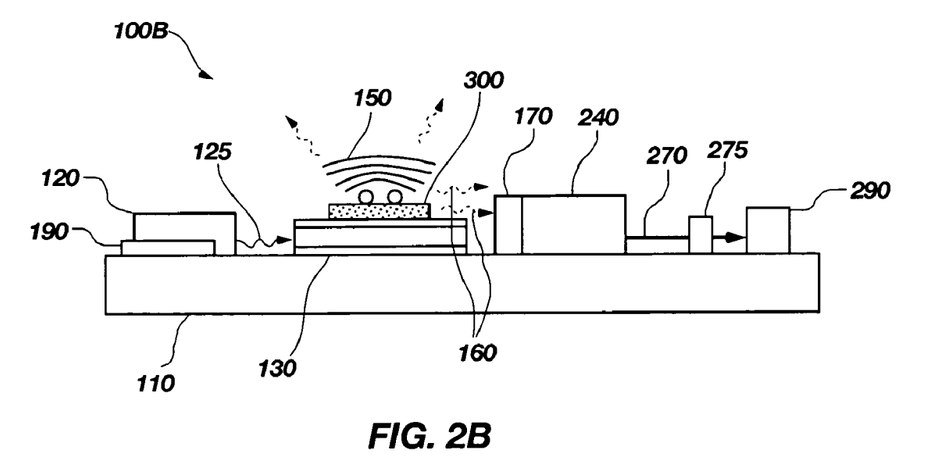
FIG. 2B is a side view of the molecular analysis device of FIG. 2A.

Similarly, FIGS. 2A and 2B illustrate another exemplary embodiment of a molecular analysis device 100B (also referred to as an evanescent irradiation device 100B). In the embodiment of FIGS. 2A and 2B, the evanescent irradiation device 100B includes the substrate 110, the laser source 120 disposed on the substrate 110, and the radiation receiver 200 disposed on the substrate 110. However, in the evanescent irradiation device 100B, a waveguide 130 may be disposed on the substrate 110 such that the waveguide 130 confines, and possibly amplifies, the laser radiation 125 from the laser source 120. The Raman enhancement structure 300 may be disposed on a surface of the waveguide 130 such that an evanescent field 150 emanating from the surface of the waveguide 130 may irradiate the Raman enhancement structure 300. An optional filter 170 may also be disposed on the substrate 110 between the Raman enhancement structure 300 and the wavelength demultiplexer 240. The evanescent irradiation device 100B may also include other optional components 190. This embodiment also may be used as a self-contained Raman spectroscopy analysis system wherein an analyte 310 may be disposed on the Raman enhancement structure 300 on the substrate 110.

Figure 3:
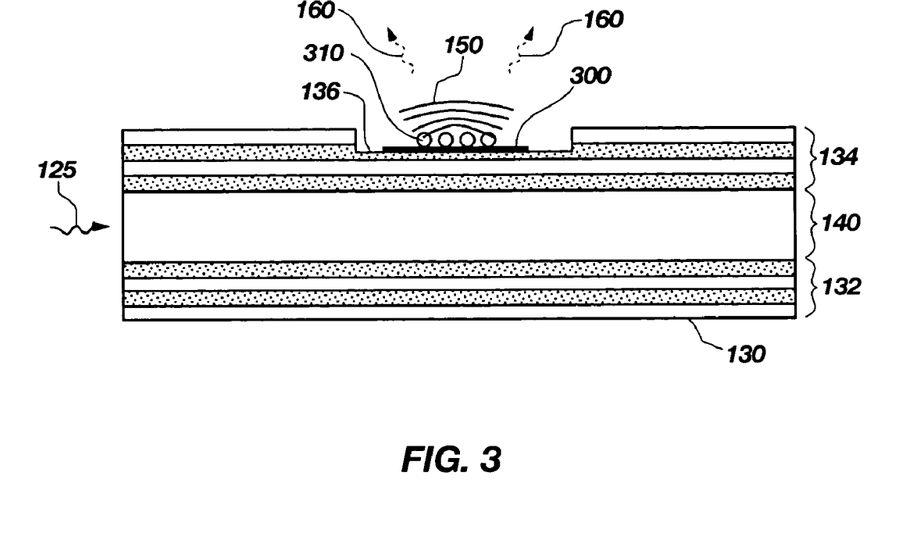
FIG. 3 is a side view of a waveguide with a depression formed therein.

The waveguide 130 used in the evanescent irradiation device 100B is shown in more detail in FIG. 3. The waveguide 130 may include a resonant cavity 140 formed between a top reflector 134 and a bottom reflector 132. In addition, if the resonant cavity 140, top reflector 134, and bottom reflector 132 are configured for a specific wavelength, the waveguide 130 may also amplify the laser radiation 125 substantially near that specific wavelength.

The top reflector 134 and bottom reflector 132 may be structures, such as, for example, distributed Bragg reflectors (also referred to as Bragg Mirrors) or distributed Bragg gratings. Bragg reflectors may be formed in a number of ways using a variety of materials configured as alternating layers; one layer with a low refractive index and the other layer with a high refractive index. Each layer is configured with a thickness of about one quarter of an odd multiple of the specific wavelength to be confined by the waveguide 130. For example, the layers may be configured with a thickness of ¼ of a wavelength or ¾ of a wavelength. The resulting Bragg reflector may also be referred to as a quarter-wave stack. As an example, a Bragg reflector may be formed from alternating layers of GaAs (gallium arsenide) and AlGaAs (aluminum gallium arsenide). Another suitable material combination for forming Bragg reflectors is alternating layers formed respectively from silicon and silicon dioxide. Implementing a larger number of alternating pairs in a Bragg reflector results in a higher refractive index. About thirty layers may create a reflectivity as high as 99.99%.

An evanescent field 150 emanating from a waveguide 130 generally decays exponentially as it emanates and propagates away from the waveguide 130. As a result, it may be desirable to form a depression 136 in the surface of the waveguide 130, as shown in FIG. 3. Forming the depression 136 may create an analysis surface in a region of increased evanescent field emanating from the waveguide 130. Accordingly, the Raman enhancement structure 300 and analyte 310 may be disposed closer to the laser source 120 where the evanescent field 150 may be stronger. However, formation and size of the depression 136 may influence the reflective properties of the waveguide 130. As a result, an optimum depression 136 depth may be determined based on desired waveguide 130 reflective properties and evanescent field 150 strength. With the depression 136 created, a Raman enhancement structure 300 may be disposed in the depression 136. For simplicity, the depression 136 is shown with a flat analysis surface and with perpendicular walls forming the sides of the depression 136. However, the depression 136 can alternatively be formed with curved walls and a flat analysis surface or as a curved analysis surface formed in the surface of the waveguide 130 using any suitable shape, such as a portion of an ellipsoid or paraboloid.

In operation of the evanescent irradiation device 100B and referring back to FIGS. 2A and 2B, either with or without the depression 136, the laser source 120 emits a laser radiation 125 in a direction such that the waveguide 130 confines, and possibly amplifies the laser radiation 125. The laser radiation 125 within the waveguide 130 may generate an evanescent field 150, which may emanate from a surface of the waveguide 130 and irradiate the Raman enhancement structure 300 and analyte 310 positioned on the waveguide 130, or within a depression 136 of the waveguide 130. In this fashion, the evanescent field 150 may irradiate the analyte 310 and Raman enhancement structure 300 across the entire length of the Raman enhancement structure 300. The irradiated combination of the Raman enhancement structure 300 and the analyte 310 may generate Raman scattered radiation 160. The Raman scattered radiation 160 may be detected as a variety of wavelengths by the radiation receiver 200, as explained more fully below.

The Raman enhancement structure 300, used in the direct irradiation device 100A and the evanescent irradiation device 100B, may be used to effect the electromagnetic enhancement of the Raman signal, chemical enhancement of the Raman signal, or both. If disposed on the substrate 110, the Raman enhancement structure 300 may be disposed through chemically bonding or, alternatively, may be disposed and weakly bonded to the substrate 110, if bonded at all. Similarly, if disposed on the waveguide 130, Raman enhancement structure 300 may be disposed by chemically bonding or, alternatively, may be disposed on the substrate 110 and weakly bonding thereto, if bonded at all.

As used herein, the term "Raman enhancement structure" 300 means any structure configured and formed of a material that may produce chemical enhancement of the Raman signal, electromagnetic enhancement of the Raman signal, or both. Exemplary materials for the Raman enhancement structure 300 include gold, silver, copper, aluminum, chromium, lithium, sodium, potassium, or any other suitable material that may produce chemical enhancement of the Raman signal, electromagnetic enhancement of the Raman signal, or both.

It has been shown that a relatively rough surface enhances the amount of Raman scattered radiation 160 that may emanate from the Raman enhancement structure 300 when an analyte 310 disposed on the Raman enhancement structure 300 is irradiated. As a result, the Raman enhancement structure 300 may be formed as a single monolithic layer, possibly with a roughened surface, or the Raman enhancement structure 300 may comprise one or more discrete particles.

As one or more discrete particles, the Raman enhancement structure 300 may have a variety of exemplary configurations, such as, nanowires (i.e., a rod shaped configuration), nanodots, nanoparticles (including employing a single nanoparticle), or metallic particles in a colloidal suspension. It is currently preferred to employ at least two silver nanoparticles spaced apart such that an analyte 310 molecule may be draped therebetween. The aforementioned nanostructures for the Raman enhancement structure 300 may be formed by chemical vapor deposition (CVD), molecular beam epitaxy (MBE), atomic layer deposition (ALD), or any other suitable technique to deposit the Raman enhancement structure 300.

The substrate 110 may be any suitable substrate 110 for bearing the laser source 120, the radiation receiver 200, and, if present, the Raman enhancement structure 300. In addition, if optional substrate 110 components are present, the substrate 110 may be selected for its properties of directing and modifying either optical signals, electrical signals, or both optical signals and electrical signals. By way of example, conventional silicon substrates as well as Class III-V materials, such as Gallium Arsenide, and Indium Phosphide may be used. In addition, the substrate 110 may be a circuit board using a material, such as, for example, FR4 circuit board material.

It may be desirable to include other optional components 190 to create an enhanced Raman spectroscopy analysis system. By way of example, Application Specific Integrated Circuits (ASIC), microprocessors, microcontrollers, digital signal processors, and discrete components may be useful. In addition, optical components such as collimators, filters, waveguides, and amplifiers may be useful. Furthermore, nanowire type sensor arrays may be desirable for verifying the presence and composition of some analytes.

The laser source 120 may be a conventional laser diode, which emits a laser radiation 125 with a wavelength that is effective for Raman spectroscopy analysis. By way of example, an edge-emitting laser diode is illustrated in the exemplary embodiments. However, other laser diode implementations are possible and encompassed by the scope of the invention, such as, for example, a Vertical Cavity Surface Emitting Laser (VCSEL). In addition, the laser diode may be integrated into the substrate 110 as part of a monolithic integration including the substrate 110 and, possibly, other optional components 190.

Similarly, the radiation receiver 200 may be disposed on the substrate 110 or may be integrated into the substrate 110 as part of a monolithic integration including the substrate 110, the laser source 120, and, possibly, other optional components 190.

The radiation receiver 200 includes a wavelength demultiplexer 240 in combination with radiation sensors 290. By demultiplexing the Raman scattered radiation 160, the unique wavelengths 260 exiting the wavelength demultiplexer 240 may be sensed by simple photodiodes responsive to a broad range of wavelengths. The photodiodes convert radiation impinging on the diode into an electrical signal proportional to the intensity of the radiation. The resulting electrical signals from all the photodiodes may be used for further analysis of the Raman spectrum.

If the wavelength demultiplexer 240 and radiation sensors 290 are separated on the substrate 110, transmission waveguides 270 may direct the unique wavelengths 260 from the wavelength demultiplexer 240 to the radiation sensors 290. In addition, if desired, optical amplifiers 275 may be implemented in the transmission waveguides 270 to amplify the unique wavelengths prior to sampling by the radiation sensors 290.

The resulting radiation receiver 200 may be configured to simultaneously detect a variety of wavelengths of Raman scattered radiation 160 such that, with a plurality of radiation sensors 290, a Raman spectrum may be obtained. The Raman spectrum may be used to determine specific analytes. In this fashion, an inexpensive molecular analysis device may be developed to detect a predetermined set of analytes.

Figure 4:
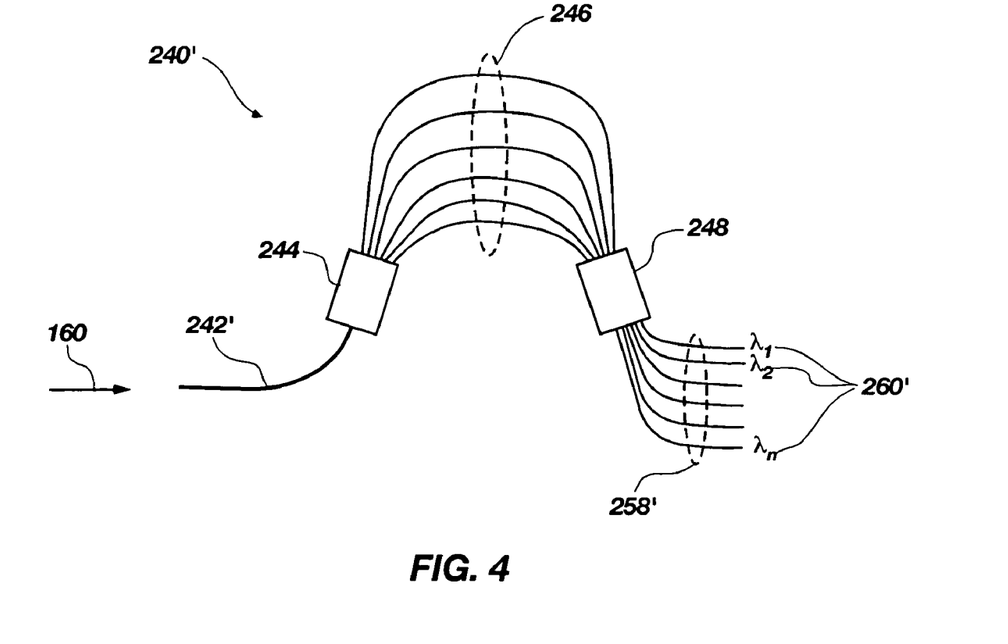
FIG. 4 is a top view of an exemplary wavelength demultiplexer employing an arrayed waveguide grating.
Figure 5:
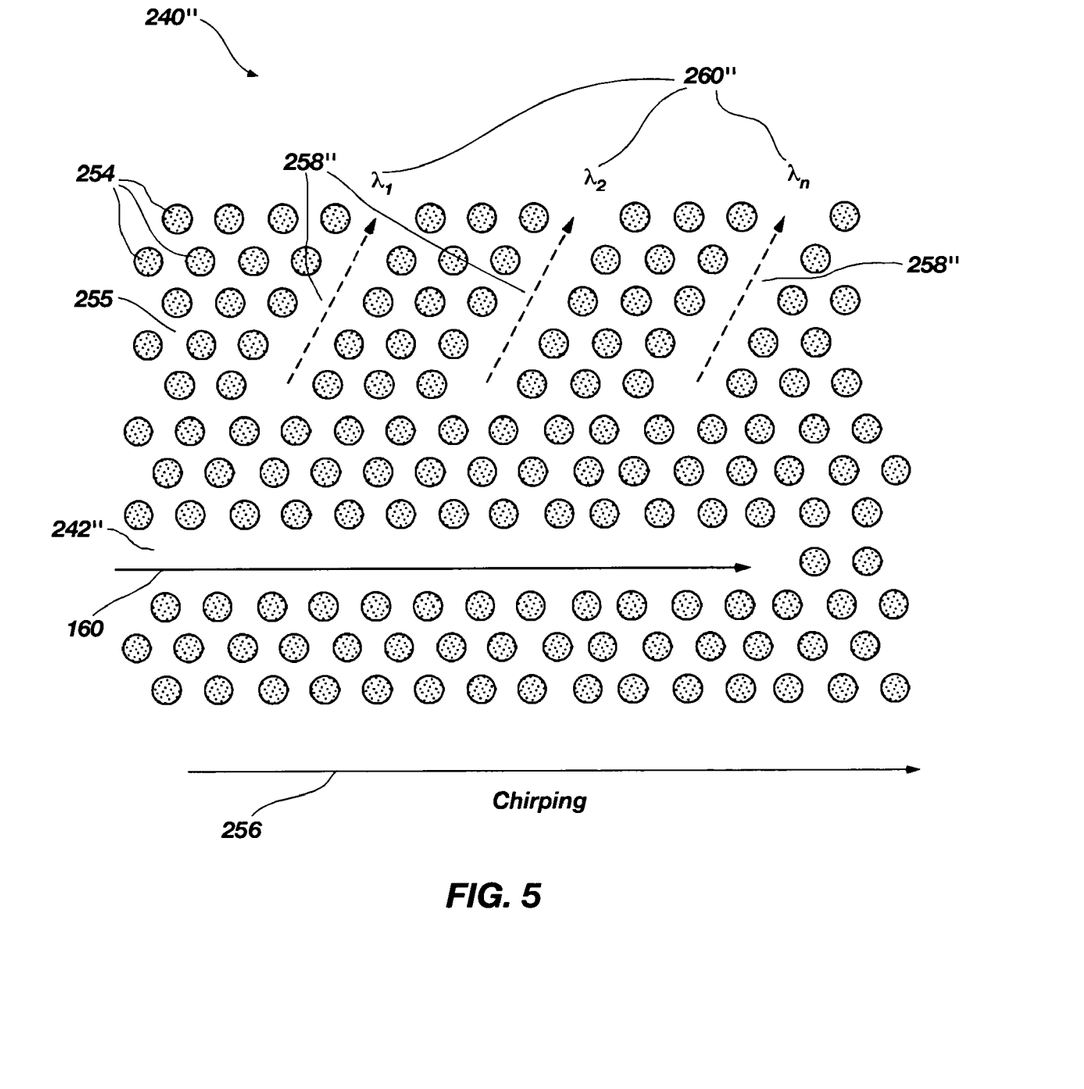
FIG. 5 is a top view of an exemplary wavelength demultiplexer employing a chirped photonic crystal.

Exemplary embodiments of a wavelength demultiplexer 240 are an Arrayed Waveguide Grating (AWG 240') element and a chirped photonic crystal 240" as shown in FIGS. 4 and 5 respectively. An AWG 240' may operate as a wavelength multiplexer and a wavelength de-multiplexer. An exemplary AWG 240' is shown in FIG. 4. A root waveguide 242' guides the Raman scattered radiation 160 to a free propagation region 244 where the Raman scattered radiation 160 may diverge to an array of waveguides 246. The array of waveguides 246 is configured such that the optical path lengths of adjacent waveguides 130 differ by about an integer multiple of the central wavelength. The individual waveguides of the array of waveguides 246 arrive at an output aperture 248 where they are recombined. Receiver waveguides (also referred to as wavelength-specific waveguides 258) are placed at a proper position along an image plane in the output aperture 248 such that spatial separation of the various wavelengths achieves the wavelength de-multiplex function. As a result, each wavelength-specific waveguide 258 carries a unique wavelength 260' out of the AWG 240'.

Another exemplary wavelength demultiplexer 240, illustrated in FIG. 5, includes a chirped photonic crystal 240". A conventional two-dimensional photonic crystal 240" material may be formed by periodically dispersing rods or columns 254 of a material of one refractive index within a matrix 255 having a different refractive index. Two-dimensional photonic crystals 240" exhibit periodicity in only two dimensions (i.e., the directions perpendicular to the length of the rods or columns 254), but no periodicity is exhibited in the direction parallel to the length of the columns 254. The photonic crystal 240" material, as shown in a top view in FIG. 5, creates a highly refractive behavior in the two dimensions of the photonic crystal 240" material. As a result, a waveguide may be created in the photonic crystal 240" by introducing a series of defects. The defects may be formed by removing or failing to form one or more columns 254 along a path for the radiation to follow. Alternatively, the defects may be formed as air gaps or as spatially confined areas of a different material, such as glass or epoxy. The defects in the photonic crystal 240" material create a waveguide along the path of the defects due to the high reflectivity in the plane perpendicular to the columns 254. For example, in the exemplary embodiment of FIG. 5, a root waveguide 242" and three wavelength-specific waveguides 258" are shown.

In addition to a conventional periodic arrangement of columns 254 forming the photonic crystal 240", a photonic crystal 240" may be formed with a "chirped" arrangement. As a chirped photonic crystal 240", the periodicity (i.e. spacing between columns 254) changes along the chirped axis 256. This chirping is useful in creating wavelength-specific waveguides 258".

As shown in FIG. 5, the photonic crystal 240" includes a chirped axis 256 substantially in a horizontal direction. In other words, the columns 254 become farther apart (or closer together) as the radiation travels from left to right along the chirped axis 256. A root waveguide 242" may carry the Raman scattered radiation 160 along this chirped axis 256. Wavelength-specific waveguides 258" may tap off at various points along the root waveguide 242. Only radiation of wavelengths substantially matching the periodicity of the columns 254 at that point along the chirped axis 256 will pass through the photonic crystal 240" and enter the wavelength-specific waveguide 258" at that location.

For simplicity, the detailed description and drawings have included three sensors and three unique wavelengths generated by the wavelength demultiplexer. It will be readily apparent to a person of ordinary skill in the art that any number of sensors and unique wavelengths may be used depending on the spectrum to be covered and the wavelengths to be detected.

Referring back to FIGS. 1A–2B, in operation of a Raman spectroscopy system, the laser source 120 irradiates the Raman enhancement structure 300 and analyte 310 (directly in the direct irradiation device 100A, or indirectly through an evanescent field 150 emanating from the waveguide 130 in the evanescent irradiation device 100B) producing an enhancement effect therein (i.e., chemical, electromagnetic, or both). In other words, irradiation of the Raman enhancement structure 300 and analyte 310 by radiation impinging on the Raman enhancement structure 300 and analyte 310, in part, produces a strong electromagnetic field in the Raman enhancement structure 300. Because the electromagnetic field is adjacent to the analyte 310, the analyte 310 is, in turn, irradiated by a very strong electromagnetic field. The irradiation of the analyte 310 by the enhanced field from the Raman enhancement structure 300 produces the aforementioned Stokes, anti-Stokes, or combined (Stokes/anti-Stokes), Raman scattered photons (also referred to as Raman scattered radiation 160) that are characteristic of the particular analyte 310 being analyzed. Because the intensity of the Raman scattered photons is, in part, proportional to the square of the electromagnetic field that irradiates the analyte 310, the enhancement effect from the Raman enhancement structure 300 may increase the intensity of the Raman signal by as much as $10^{14}$.

Some of the Raman scattered radiation 160 may be detected by the radiation receiver 200. The wavelength demultiplexer 240 separates the Raman scattered radiation 160 into a plurality of unique wavelengths 260, which are sensed by radiation sensors 290. The radiation sensors 290 convert the intensity detected into electrical signals.

If used for hyper-Raman spectroscopy, when excitation radiation impinges on an analyte molecule, a small number of photons may be scattered at frequencies corresponding to the higher order harmonics of the excitation radiation, such as the second and third harmonics (i.e., twice or three times the frequency of the excitation radiation). Some of these photons may be Raman scattered photons with a frequency that is Raman-shifted relative to the frequencies corresponding to the higher order harmonics of the excitation radiation. Therefore, in hyper-Raman spectroscopy, as examples and not limitations of higher order harmonics, the incident excitation photons may have approximately ½, ⅓, or ¼, the frequency of the Raman photons.

This hyper-Raman excitation has the added advantage that the excitation frequency and Rayleigh scattered radiation at the excitation frequency may be easily filtered out from the Raman signal frequency by an inexpensive optical filter 170. In this invention, we define ERS to include Raman, hyper-Raman and higher multiple excitation photons.

For illustration of a specific example, and not a limitation, the excitation photon may have a wavelength of about 980 nm, and the Raman signal may have wavelengths of about 490 nm. As a result, the filter 170 may be configured to substantially filter out the radiation at and near the 980 nm wavelength, while passing the shorter wavelengths. Alternatively photodiodes comprising GaN/InGaN/AlGaN, which are transparent to 980 nm but detect frequencies near 490 nm may be used.

The electrical signals from either embodiment may be directed to electronic equipment apart from the molecular analysis device 100 or may be directed to other optional components 190 on the substrate 110 for development of a Raman spectrum, which may be used to identify a specific analyte 310.

Specific configurations of the wavelength demultiplexer 240 relative to the Raman enhancement structure 300 are shown in the drawings. However, because the Raman scattering is generally isotropic, (i.e., being scattered in all directions), many other locations of the Raman enhancement structure 300 relative to the wavelength demultiplexer 240 are contemplated and within the scope of the present invention.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A molecular analysis device, comprising:
   a substrate;
   a laser source disposed on the substrate and configured for generating a laser radiation with a direction substantially parallel with the substrate;
   a Raman enhancement structure disposed on the substrate with an active surface substantially parallel to the substrate, the Raman enhancement structure configured for producing a Raman scattered radiation when the laser radiation irradiates an analyte disposed on the Raman enhancement structure;
   a wavelength demultiplexer disposed on the substrate and configured for dispersing the Raman scattered radiation into at least two unique wavelengths; and
   at least two radiation sensors disposed on the substrate, each radiation sensor configured for sensing one of the at least two unique wavelengths.

2. The molecular analysis device of claim 1, wherein the laser radiation comprises a wavelength that is an integer multiple of a wavelength substantially near the Raman scattered radiation.

3. The molecular analysis device of claim 2, further comprising a filter disposed between the Raman enhancement structure and the wavelength demultiplexer, the filter configured for substantially filtering out radiation substantially near the wavelength of the laser radiation.

4. The molecular analysis device of claim 1, wherein the substrate, the laser source, the Raman enhancement structure, the wavelength demultiplexer, and the at least two radiation sensors comprise a monolithic integration.

5. The device of claim 1, wherein the wavelength demultiplexer comprises a chirped photonic crystal, the chirped photonic crystal comprising:
   a root waveguide configured for receiving and guiding the Raman scattered radiation; and
   at least two wavelength-specific waveguides, each wavelength-specific waveguide disposed at a position along a chirped axis correlated with one of the at least two unique wavelengths and each wavelength-specific waveguide configured for guiding one of the at least two unique wavelengths.

6. The device of claim 1, wherein the wavelength demultiplexer comprises an arrayed waveguide grating.

7. The device of claim 1, further comprising at least two transmission waveguides, each transmission waveguide configured for guiding one of the at least two unique wavelengths between the wavelength demultiplexer and one of the at least two radiation sensors.

8. The device of claim 7, further comprising at least two optical amplifiers, each optical amplifier disposed within one of the at least two transmission waveguides and configured for amplifying the unique wavelength guided by the one of the at least two transmission waveguides.

9. The device of claim 1, wherein the Raman enhancement structure comprises a metallic material selected from the group consisting of gold, silver, copper, aluminum, chromium, lithium, sodium, and potassium.

10. The device of claim 9, wherein the Raman enhancement structure is substantially roughened to increase a surface enhancement effect of the Raman scattered radiation.

11. The device of claim 1, wherein the Raman enhancement structure comprises a plurality of nanostructures including a metallic material, wherein the plurality of nanostructures are selected from the group consisting of nanodots and nanowires.

12. The device of claim 11, wherein the metallic material is selected from the group consisting of gold, silver, copper, aluminum, chromium, lithium, sodium, and potassium.

13. The device of claim 1, wherein the Raman enhancement structure comprises a colloid containing metallic particles, wherein the metallic particles are selected from the group consisting of gold, silver, copper, aluminum, chromium, lithium, sodium, and potassium.

14. A molecular analysis device, comprising:
   a substrate;
   a laser source disposed on the substrate, and configured for generating a laser radiation with a direction substantially parallel with the substrate;
   a waveguide disposed on the substrate and configured for generating an evanescent field when the laser radiation is present in the waveguide;
   a Raman enhancement structure disposed on the waveguide and configured for producing a Raman scattered radiation when the evanescent field irradiates an analyte disposed on the Raman enhancement structure; and
   a wavelength demultiplexer disposed on the substrate and configured for dispersing the Raman scattered radiation into at least two unique wavelengths; and
   at least two radiation sensors disposed on the substrate, each radiation sensor configured for sensing one of the at least two unique wavelengths.

15. The molecular analysis device of claim 14, wherein the laser radiation comprises a wavelength that is an integer multiple of a wavelength substantially near the Raman scattered radiation.

16. The molecular analysis device of claim 15, further comprising a filter disposed between the Raman enhancement structure and the wavelength demultiplexer, the filter configured for substantially filtering out radiation substantially near the wavelength of the laser radiation.

17. The molecular analysis device of claim 14, wherein the substrate, the laser source, the waveguide, the Raman enhancement structure, the wavelength demultiplexer, and the at least two radiation sensors comprise a monolithic integration.

18. The molecular analysis device of claim 14, wherein:
   the waveguide further comprises a depression formed in the waveguide exposing a region of increased evanescent field, the increased evanescent field being generated when the laser radiation is present in the waveguide, and
   the Raman enhancement structure is disposed in the depression of the waveguide.

19. The device of claim 14, wherein the wavelength demultiplexer comprises a chirped photonic crystal, the chirped photonic crystal comprising:
   a root waveguide configured for receiving and guiding the Raman scattered radiation; and
   at least two wavelength-specific waveguides, each wavelength-specific waveguide disposed at a position along a chirped axis correlated with one of the at least two unique wavelengths and each wavelength-specific waveguide configured for guiding one of the at least two unique wavelengths.

20. The device of claim 14, wherein the wavelength demultiplexer comprises an arrayed waveguide grating.

21. The device of claim 14, further comprising at least two transmission waveguides, each transmission waveguide configured for guiding one of the at least two unique wavelengths between the wavelength demultiplexer and one of the at least two radiation sensors.

22. The device of claim 21, further comprising at least two optical amplifiers, each optical amplifier disposed within one of the at least two transmission waveguides and configured for amplifying the unique wavelength guided by the one of the at least two transmission waveguides.

23. The device of claim 14, wherein the Raman enhancement structure comprises a metallic material selected from the group consisting of gold, silver, copper, aluminum, chromium, lithium, sodium, and potassium.

24. The device of claim 23, wherein the Raman enhancement structure is substantially roughened to increase a surface enhancement effect of the Raman scattered radiation.

25. The device of claim 14, wherein the Raman enhancement structure comprises a plurality of nanostructures including a metallic material, wherein the plurality of nanostructures are selected from the group consisting of nanodots and nanowires.

26. The device of claim 25, wherein the metallic material is selected from the group consisting of gold, silver, copper, aluminum, chromium, lithium, sodium, and potassium.

27. The device of claim 14, wherein the Raman enhancement structure comprises a colloid containing metallic particles, wherein the metallic particles are selected from the group consisting of gold, silver, copper, aluminum, chromium, lithium, sodium, and potassium.

28. A method of performing Raman spectroscopy, comprising:
   generating a laser radiation from a laser source disposed on a substrate, the laser radiation having a direction substantially parallel with the substrate and a Raman enhancement structure disposed over at least a portion of the substrate such that the laser radiation is directed over a surface of the Raman enhancement structure;
   disposing an analyte over at least a portion of the Raman enhancement structure;
   irradiating the analyte and the Raman enhancement structure with the laser radiation to generate a Raman scattered radiation;
   dispersing the Raman scattered radiation into at least two unique wavelengths; and
   sensing the at least two unique wavelengths with at least two radiation sensors disposed on the substrate.

29. The method of claim 28, further comprising generating a wavelength of the laser radiation that is an integer multiple of a wavelength substantially near the Raman scattered radiation.

30. The method of claim 29, further comprising filtering the Raman scattered radiation to substantially remove radiation substantially near the wavelength of the laser radiation.

31. The method of claim 28, wherein dispersing the Raman scattered radiation further comprises:
   receiving the Raman scattered radiation in a root waveguide of a chirped photonic crystal;
   positioning at least two wavelength-specific waveguides in the chirped photonic crystal, each wavelength-specific waveguide positioned along a chirped axis correlated with one of the at least two unique wavelengths; and
   guiding each of the at least two unique wavelengths through each of the two wavelength-specific waveguides.

32. The method of claim 28, wherein dispersing the Raman scattered radiation is performed by an arrayed waveguide grating.

33. The method of claim 28, further comprising guiding each of the at least two unique wavelengths between a wavelength demultiplexer and one of at least two sensors.

34. The method of claim 28, further comprising generating at least one amplified unique wavelength by amplifying at least one of the at least two unique wavelengths and sensing the at least one amplified unique wavelength with at least one of the at least two radiation sensors.

35. The method of claim 28, further comprising disposing the Raman enhancement structure on the substrate.

36. The method of claim 28, wherein disposing the analyte comprises disposing at least one molecule of the analyte.

37. The method of claim 28, further comprising, selecting the Raman enhancement structure to comprise a metallic material selected from the group consisting of gold, silver, copper, aluminum, chromium, lithium, sodium, and potassium.

38. The method of claim 28, further comprising, selecting the Raman enhancement structure to comprise a colloid including metallic particles selected from the group consisting of gold, silver, copper, aluminum, chromium, lithium, sodium, and potassium.

39. The method of claim 28, further comprising, selecting the Raman enhancement structure to comprise at least one particle in the form of a nanodot or a nanorod.

40. A method of performing Raman spectroscopy, comprising:
   generating a laser radiation from a laser source disposed on a substrate, the laser radiation directed at a waveguide disposed on at least a portion of the substrate, the waveguide being substantially parallel with the substrate;
   disposing an analyte over at least a portion of a Raman enhancement structure, the Raman enhancement structure disposed on at least a portion of a surface of the waveguide;
   generating an evanescent field emanating from the surface of the waveguide by irradiating the waveguide with the laser radiation, the evanescent field irradiating the analyte and the Raman enhancement structure to generate a Raman scattered radiation;
   dispersing the Raman scattered radiation into at least two unique wavelengths; and
   sensing the at least two unique wavelengths with at least two radiation sensors disposed on the substrate.

41. The method of claim 40, further comprising generating a wavelength of the laser radiation that is an integer multiple of a wavelength substantially near the Raman scattered radiation.

42. The method of claim 41, further comprising filtering the Raman scattered radiation to substantially remove radiation substantially near the wavelength of the laser radiation.

43. The method of claim 40, wherein generating the evanescent field further comprises generating an increased evanescent field in the region of a depression formed in the waveguide.

44. The method of claim 40, wherein dispersing the Raman scattered radiation further comprises:
   receiving the Raman scattered radiation in a root waveguide of a chirped photonic crystal;
   positioning at least two wavelength-specific waveguides in the chirped photonic crystal, each wavelength-specific waveguide positioned along a chirped axis correlated with one of the at least two unique wavelengths; and guiding each of the at least two unique wavelengths through each of the two wavelength-specific waveguides.

45. The method of claim 40, wherein dispersing the Raman scattered radiation is performed by an arrayed waveguide grating.

46. The method of claim 40, further comprising guiding each of the at least two unique wavelengths between a wavelength demultiplexer and one of at least two sensors.

47. The method of claim 40, further comprising generating at least one amplified unique wavelength by amplifying at least one of the at least two unique wavelengths and sensing the at least one amplified unique wavelength with at least one of the at least two radiation sensors.

48. The method of claim 40, further comprising disposing the Raman enhancement structure on the substrate.

49. The method of claim 40, wherein disposing the analyte comprises disposing at least one molecule of the analyte.

50. The method of claim 40, further comprising, selecting the Raman enhancement structure to comprise a metallic material selected from the group consisting of gold, silver, copper, aluminum, chromium, lithium, sodium, and potassium.

51. The method of claim 40, further comprising, selecting the Raman enhancement structure to comprise a colloid including metallic particles selected from the group consisting of gold, silver, copper, aluminum, chromium, lithium, sodium, and potassium.

52. The method of claim 40, further comprising, selecting the Raman enhancement structure to comprise at least one particle in the form of a nanodot or a nanorod.

* * * * *